United States Patent
Xu et al.

(10) Patent No.: US 10,508,132 B2
(45) Date of Patent: Dec. 17, 2019

(54) METHOD FOR PRODUCING AEROBIC-TYPE SINGLE CELL PROTEIN USING THE AUTOLYSIS PROCESS

(71) Applicant: Taizhou iCell Bio-Tech Co., Ltd., Taizhou (CN)

(72) Inventors: Jiangang Xu, Taizhou (CN); Jianhua Song, Taizhou (CN); Weiwei Zhao, Taizhou (CN); Xinjie Zhang, Taizhou (CN)

(73) Assignee: Taizhou iCell Bio-Tech Co., Ltd., Taizhou (CN)

( * ) Notice: Subject to any disclaimer, the term of this patent is extended or adjusted under 35 U.S.C. 154(b) by 984 days.

(21) Appl. No.: 14/901,511

(22) PCT Filed: Apr. 7, 2015

(86) PCT No.: PCT/CN2015/075972
§ 371 (c)(1),
(2) Date: Dec. 28, 2015

(87) PCT Pub. No.: WO2016/161549
PCT Pub. Date: Oct. 13, 2016

(65) Prior Publication Data
US 2017/0037081 A1   Feb. 9, 2017

(51) Int. Cl.
*C07K 1/14* (2006.01)
*C12N 1/06* (2006.01)
*A23J 1/00* (2006.01)

(52) U.S. Cl.
CPC .............. *C07K 1/14* (2013.01); *A23J 1/008* (2013.01); *C12N 1/06* (2013.01)

(58) Field of Classification Search
None
See application file for complete search history.

(56) References Cited

U.S. PATENT DOCUMENTS

| 7,700,140 B2 * | 4/2010 | Moen | A23K 40/20 426/53 |
| 2004/0265431 A1 * | 12/2004 | Kleppe | A23K 50/80 426/61 |

* cited by examiner

*Primary Examiner* — Robert J Yamasaki
(74) *Attorney, Agent, or Firm* — CBM Patent Consulting, LLC

(57) ABSTRACT

A method for producing aerobic-type single cell protein using the autolysis process, comprising the following steps: precipitation and concentration, centrifugal dewatering, drying, sterilization, smashing and packaging. The materials with moisture content of 78%~85% after centrifugal dewatering are dried after the autolysis. The present invention and its products employ the autolysis process. During the autolysis, macromolecular nutrients and cell walls are decomposed by autolytic enzymes, to produce high content of free amino acids, free nucleotides; besides, cell wall polysaccharides are decomposed and the cells produce permeability to ensure an active material can flow out of the cell which can be directly absorbed by animals.

3 Claims, 7 Drawing Sheets

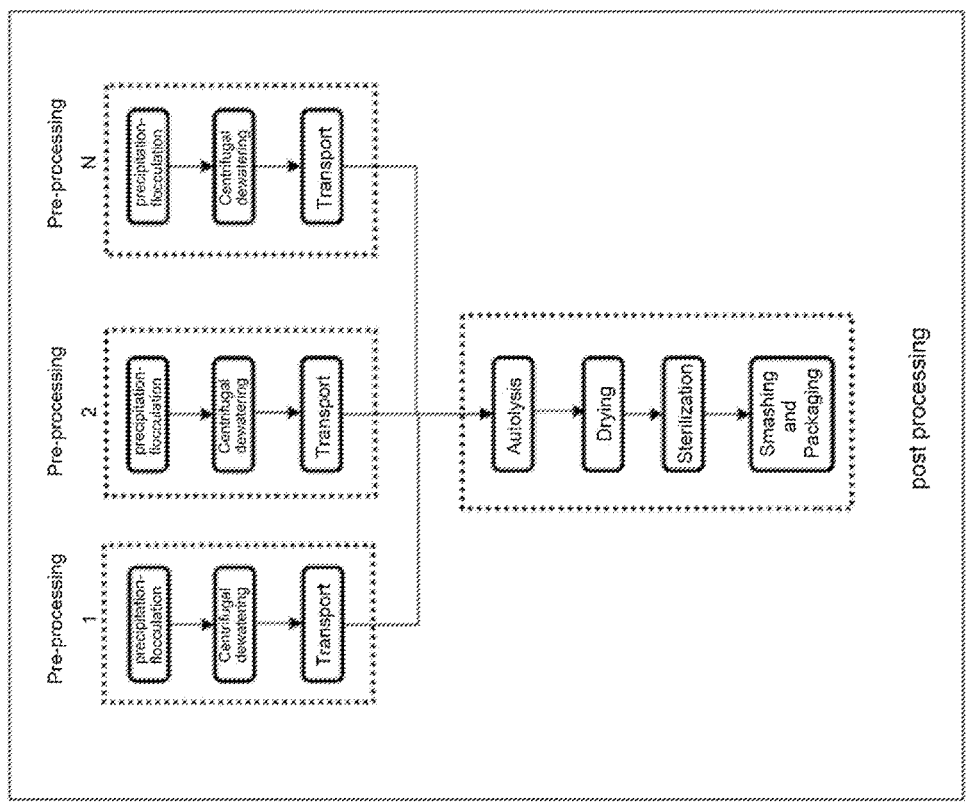
FIG. 4
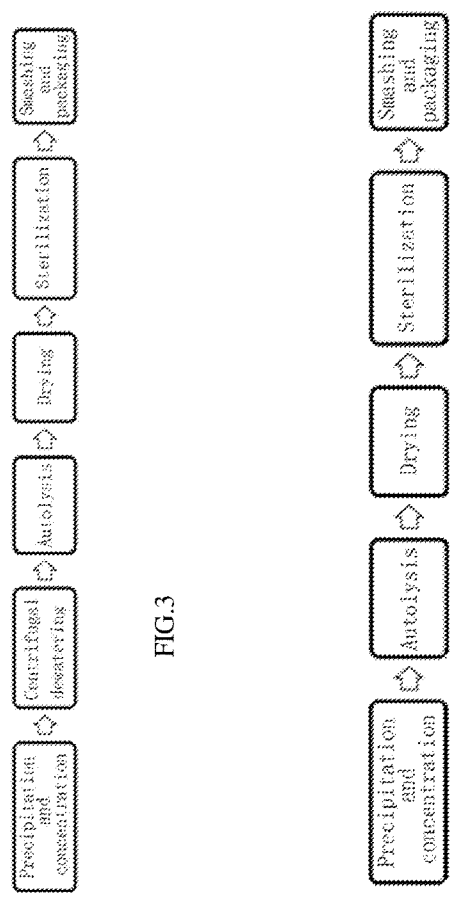
FIG. 3
FIG. 5

METHOD FOR PRODUCING AEROBIC-TYPE SINGLE CELL PROTEIN USING THE AUTOLYSIS PROCESS

This application is the U.S. national phase of International Application No. PCT/CN2015/075972 Filed on 7 Apr. of 2015 which designated the U.S., the entire content of which is hereby incorporated by reference.

TECHNICAL FIELD

The present invention relates to the single cell protein processing technology, in particular, to a method for producing aerobic-type single cell protein using the autolysis process.

BACKGROUND ART

Single cell protein (Single cell protein, SCP), also known as microbial protein or bacterial protein, is made by the single cell organisms such as cultured yeast, non-pathogenic bacteria, micro-bacteria, fungi after purification and drying using the industrial waste water, waste gas, natural gas, petroleum hydrocarbons, agro-processed products and organic wastes as the medium. It is an important source of protein in food and feed industries. SCP products are rich in protein, with full range of amino acids at appropriate proportions. SCP is also rich in fats, carbohydrates, nucleic acids, vitamins and inorganic salts, and contains a variety of mineral elements such as calcium, phosphorus, potassium, iron, magnesium, sodium, manganese, and a variety of enzymes. Yeast, yeast hydrolyzates have been successfully used as substitutes of fish meal protein in the animal feeds, which can enhance animal immunity and improve the taste of feeds, etc., SCP nucleotide and its derivatives have very important physiological and biochemical functions, mainly as follows: the raw material of RNA and DNA synthesis; the regulatory substance of metabolism; the ingredients of coenzyme, such as coenzyme A; important intermediary for activation of glycogen and glycoproteins synthesis, the intermediary of phospholipid synthesis, activation of intermediate products; participation in genetic information transfer; ATP is the direct energy of life process; AMP can regulate the smooth muscle contractility and blood flow; and nucleotides can be used as the donor of methyl, etc.

Since the harmful microbes, harmful chemicals, heavy metals may influence the product quality and safety, there are fewer varieties of SCP products that have been developed or are under industrial development. It mainly focuses on the culture and production of SCP using the product or by-product from the food industry with low safety risk as the raw material, for example, the use of beer yeast and zymolytic beer yeast as feed ingredients in animals. The beer production process should meet the strict food safety standards, and the biological, chemical and physical hazards of organic byproducts and yeast proteins produced should be minimized, to provide reliable safety guarantee for its applications in the feed industry.

Patent WO2009059163A1 provides a method for the culture of SCP. The cultured SCP can be used as excellent protein source of animal feeds. This technology adopts the wastewater producing in the food or beverage processing factory such as brewery as the liquid culture medium of the bacteria. The beverage wastewater has rich organic matter, nitrogen and phosphorus and other nutrients, and has no contamination of harmful microorganisms, toxic chemicals. Although these wastewater is of no value for the beverage factory and the treatment of the wastewater containing organic matter and nitrogen and phosphorus will cost much, the wastewater nutrients can become nutrient-rich medium from the perspective of the microbial culture, which can be used to produce special SCP. According to the patent WO2009059163A1, the SCP products with high protein content and high nutritional value are produced with the genetically modified bacteria through adjusting the ratio of various nutrients in the wastewater. The SCP is a mixture of bacteria, mainly containing *Micrococcus, Bacillus* bacteria, nitrifying bacteria, *Alcaligenes* and other aerobic bacteria. Meanwhile, the nutrient content in the beverage wastewater will be reduced after culture of microbes, which reduce the level of water pollution. This patented technology can achieve the production of high-quality protein and reduce the concentration of organic matter in wastewater to below the legal standard, having both economical and environmental values. Thus, this technology has a very good industrial prospect. Since the bacterial growth cycle is short and the nutrient use efficiency is high, the yield of SCP culture is very high, which provides an economic guarantee for the industrialization. However, the solids content is very low in the culture due to the bacterial growth characteristics, usually lower than 4000 mg/L. If the SCP is processed into the finished product, it is necessary to consider how to extract the SCP from water and process them to dry product with low moisture content at a low cost. Based on the characteristics of SCP as described in the patent WO2009059163A1, the existing processing technology has the following drawbacks:

1) The processing technology only uses the SCP as ordinary protein for the production, mainly focuses on the protein dehydration, drying, sterilization, to produce the protein, without considering that the bacteria in the patent WO2009059163A1 can be used to produce high quality of product using further processing techniques;

2) The SCP cultured by the patent WO2009059163A1 contains a large amount of endogenous enzymes after study, specifically including nuclease, protease and lysozyme. These enzymes can decompose macromolecular nutrients. Therefore, by using the autolysis technique, a number of active substances can be decomposed from the endogenous enzymes of bacteria, such as free amino acids, nucleotides, monosaccharides and so on. However, according to the existing process, the direct drying and microwave sterilization after dewatering has destroyed most of the endogenous enzymes, therefore, it will not produce active substances;

3) The protein digestibility is still not high based on the existing process, which need to be further improved;

4) SCP has high content of nucleic acids. The nucleic acids are not decomposed to nucleotides and still in the cell after ordinary drying process. But through a certain method, nucleic acids can be decomposed to nucleotides; and SCP can have the food calling and immunity effect when used as the animal feeds. The existing process fails to consider how to decompose nucleic acids to nucleotides with high value.

5) Although the yield of cultured SCP is very high, the production capacity of the subsequent processing equipment still can be significantly higher than that of the cultured SCP, for example, in the patent CN2014100556582, restricted by the cultured low output and even cannot reaching the average capacity of equipment, which causes the wastes of the invested equipments.

Chinese Patent (No. 201410055658.2) discloses a method for producing SCP powder using biological mud. It is a recycling method with biological mud to produce SCP. After concentration of the biological mud discharged from biological farming system, then centrifugal dewatering, instant hot air drying, cooling and microwave sterilization are performed, to get crude SCP powder. This patent is a prior application of our company, but the cell protein utilization efficiency is low due to lack of autolysis process. Autolysis refers to a process that in vivo macromolecular substances of bacteria are hydrolyzed to amino acids, nucleotides, monosaccharide and other small molecules by using their own endogenous enzymes (proteases, nucleases, lysozyme, etc.). Autolysis is a complex process, affected by a variety of factors, including the bacterial species, moisture content, temperature, pH, time, type of endogenous enzymes, etc., More importantly, autolysis is not a single process under the natural condition. It is a process before dead living body becomes decayed. The macromolecules are decomposed to amino acids, nucleotides and other nutrients after autolysis, which provides important source of nutrition for the growth of spoilage microbes. Therefore, the results of autolysis are different due to the species of microbes, autolysis conditions, and target products, etc., moreover, the autolysis failure will result in the production of spoilage products such as ammonia, hydrogen sulfide, trimethylamine, etc.

Chinese patents (patent numbers 2008800240991 and 2011102810796) disclose the production of yeast autolysate using the autolysis process, to improve the product flavor. But the two patents are not applicable to this patent. Raw materials used in the two patents are anaerobic bacteria, which have greatly different characteristics from aerobic bacteria, and their autolysis ways are also different, for example, the time of autolysis of anaerobic bacteria is longer, and enzymes should be added to promote autolysis; autolysis of anaerobic bacteria is restricted by reaction vessel, moisture content, pH, temperature, etc., and the products are difficult to control, easy to produce high content of decayed products.

SUMMARY OF THE INVENTION

The object of the invention is to overcome the above shortcomings and defects and provide a method for producing aerobic-type single cell protein using autolysis process with high-quality active ingredients.

In order to achieve the above objectives, the present invention designs a method for producing aerobic-type single cell protein using the autolysis process, comprising the following steps: precipitation and concentration, centrifugal dewatering, drying, sterilization, smashing and packaging, wherein the materials with 78%~85% moisture content after centrifugal dewatering are dried after the autolysis and the said autolysis steps are as follows:
  a) The autolysis device is heated by the twin-screw hollow blades to reach the temperature of autolysis, and through designing and adjusting the chamber volume matching the feeding speed, to meet the requirement of autolysis time;
  b) the front ¼ to ½ of the said twin-screw front hollow blade of autolysis device is the heating section, for the purpose of heating the materials to the temperature required for autolysis, the remaining section is the holding section, to maintain the temperature of the autolysis of materials;
  c) the temperature of autolysis: the temperature of the material after heating is maintained at 65° C.~95° C.;
  d) The time of autolysis: the time for the heating section to rise to the target temperature should be less than 30 min, and the time of autolysis of the holding section should be 30 min~360 min;

The moisture content of the materials: The moisture content of the material after autolysis should be no less than 70%;

The said sterilization step adopts microwave sterilization.

The temperature of materials after heating should be maintained at 65° C.~80° C. and the time of autolysis is 1~3 hours.

The specific steps are as follows:
  (1) Precipitation and concentration: The bacterial proteins generating from the bioreactor are delivered to the settling thickener, and the bacterial proteins are precipitated at the bottom of the conical concentration tank. The material moisture content at the bottom is reduced to 97% or less for the subsequent dewatering process;
  (2) convey the materials at the bottom of concentration tank to the centrifugal dewatering equipment using a transfer pump;
  (3) Centrifugal dewatering: perform solid-liquid separation using the horizontal spiral centrifuge. After centrifugation, the material moisture content is reduced to 78% to 85% and the materials are mud-like. The water after centrifugation is the extracellular water of bacterial protein, and the intracellular water still remain in the cell, which creates conditions for the autolysis of intracellular endogenous enzymes. After centrifugation, the materials with moisture content 78% ~85% can have autolysis;
  (4) Autolysis: The materials that extracellular water is removed by centrifuge are conveyed to the autolysis device for autolysis treatment;
    a) the autolysis device is heated through the twin-screw hollow blades to reach the temperature for autolysis. By designing and adjusting the volume of chamber matching the feeding speed, the time of autolysis can be achieved;
    b) the said autolysis device employs the HT fluid or steam for heating the hollow blades;
    c) The front ¼ to ½ section of the twin-screw hollow blades of the autolysis device is the heating section, which is to heat materials to the required temperature, and the remaining section is the holding section, to maintain the autolysis temperature of materials;
    d) The autolysis temperature: the temperature of material after heating is maintained at 65° C.~95° C.;
    e) Autolysis time: the time for the heating section to heat the materials to the target temperature should be less than 30 min, and the autolysis time in the holding section should be 30 min~360 min;
    f) The moisture for materials: the material moisture content after autolysis should not be less than 70%;
  (5) Drying: The materials after autolysis are conveyed to air flash drying equipment for drying through an auger feeder; and the said flash-dried material contact temperature should be less than 100° C. and the moisture content of material after drying should be 10%~40%;
  (6) Sterilization: The dried materials are conveyed to a tunnel type microwave drying sterilization equipment for sterilization by airflow lifting equipment; and the said materials after microwave sterilization have the moisture content at 5%~10%;
  (7) Smashing and packaging: The sterilized materials can be packaged to finished products after smashing.

A method for producing aerobic-type single cell protein using the autolysis process, comprising several pre-processing units and a post-processing unit, pre-processing unit includes the steps of precipitation and concentration, centrifugal dewatering and transport, wherein the materials with moisture content of 78%~85% obtained after centrifugal dewatering are cooled down and transported to the post-processing unit for centralized processing in each pre-processing unit, and the said post-processing unit includes the steps of autolysis, drying, sterilization, smashing and packaging. The said autolysis steps are as follows:

a) materials from the pre-processing unit are delivered to insulation silo, and then delivered to autolysis equipment for autolysis treatment;

b) the autolysis device is heated through the twin-screw hollow blades to reach the temperature for autolysis. By designing and adjusting the volume of chamber matching the feeding speed, the time of autolysis can be achieved;

c) The front ¼ to ½ section of the twin-screw hollow blades of the autolysis device is the heating section, which is to heat materials to the required temperature, and the remaining section is the holding section, to maintain the autolysis temperature of materials;

d) the autolysis temperature: the temperature of material after heating is maintained at 65° C. ~95° C.;

e) autolysis time: the time for the heating section to heat the materials to the target temperature should be less than 30 min, and the autolysis time in the holding section should be 30 min~360 min;

The moisture for materials: the material moisture content after autolysis should not be less than 70%;

The sterilization adopts the microwave sterilization.

The temperature of materials after heating should be maintained at 65° C.~80° C. and the time of autolysis is 60~180 minutes.

The specific method and steps are as follows:

(1) Pre-processing unit:

a. Precipitation and concentration: The bacterial proteins generating from the bioreactor are delivered to the settling thickener, and the bacterial proteins are precipitated at the bottom of the conical concentration tank. The material moisture content at the bottom is reduced to 97% or less for the subsequent dewatering process;

b. convey the materials at the bottom of concentration tank to the centrifugal dewatering equipment using a transfer pump;

c. Centrifugal dewatering: perform solid-liquid separation using the horizontal spiral centrifuge. After centrifugation, the material moisture content is reduced to 78% to 85% and the materials are mud-like. The water after centrifugation is the extracellular water of bacterial protein, and the intracellular water still remain in the cell, which creates conditions for the autolysis of intracellular endogenous enzymes. After centrifugation, the materials with moisture content 78%~85% can have autolysis;

d. Transport: Materials after centrifugation are transported to the post-processing unit for centralized treatment after cooling; the said cooling is to cool down the materials below 10° C. The said transport is to transport the mud-like materials producing in the pre-processing unit to the post-processing unit for subsequent processing; the time of said transport should be within 0~12 hours, and the temperature of materials arriving at the post-processing unit is no higher than the temperature when leaving the pre-processing unit by 5° C.;

(2) Post-processing unit:

a. autolysis: materials from the pre-processing unit are delivered to insulation silo, and then delivered to autolysis equipment for autolysis treatment; the autolysis device is heated through the twin-screw hollow blades to reach the temperature for autolysis. By designing and adjusting the volume of chamber matching the feeding speed, the time of autolysis can be achieved; The front ¼ to ½ section of the twin-screw hollow blades of the autolysis device is the heating section, which is to heat materials to the required temperature, and the remaining section is the holding section, to maintain the autolysis temperature of materials; the autolysis temperature: the temperature of material after heating is maintained at 65° C.~95° C.; Autolysis time: the time for the heating section to heat the materials to the target temperature should be less than 30 min, and the autolysis time in the holding section should be 30 min~360 min; The moisture for materials: the material moisture content after autolysis should not be less than 70%;

b. Drying: The materials after autolysis are conveyed to air flash drying equipment for drying through an auger feeder; and the said flash-dried material contact temperature should be less than 100° C. and the moisture content of material after drying should be 10%~40%;

c. Sterilization: The dried materials are conveyed to a tunnel type microwave drying sterilization equipment for sterilization by airflow lifting equipment; and the said materials after microwave sterilization have the moisture content at 5%~10%;

d. Smashing and packaging: The sterilized materials can be packaged to finished products after smashing.

The above two kinds of autolysis device comprises a pulley, a reducer, a transmission gear, a cover plate, a feeding port, heating hollow blades, insulation hollow blades, overflow plate, discharge port, import and export of steam, motor, host housing and drive spindle. The host housing is equipped with the cover plate at the top and drive spindle inside. The drive spindle is provided with twin-screw hollow blades, the cover plate is provided with feeding port; at the bottom of host housing is provided with a discharge port. An overflow plate is provided in the host housing close to the discharge port. One end of the drive spindle is connected to the transmission gear, which is engaged with the gear at the reduction gear output end. The input end of the reduction gear is connected to the output end of the motor via belt pulley, and the other end of the drive spindle is connected to the inlet and outlet of the steam or HT fluid. The front ¼-½ of the said twin-screw hollow blade is the heating section and the remaining section is the holding section. Two drive spindles and two twin-screw hollow blades are provided inside the host housing.

A method for producing aerobic-type single cell protein using autolysis process, comprising following steps: precipitation and concentration, drying, sterilization, and smashing and packaging, wherein the bacterial protein producing from bioreactor can be drained to settling thickener and the bacterial protein is precipitated at the bottom of the conic concentration tank. The moisture content of materials at the bottom is reduced to 97~98%. The materials at the bottom of the concentration tank are delivered to the autolysis device using transfer pump for autolysis. The autolysis steps are as follows:

a) the said autolysis device is a vertical enzymatic reaction tank, by introducing he steam to the hydrolysis tank interlayer, it can achieve rapid heating, and then changing to injecting low-pressure steam for autolysis reaction;

b) the said autolysis device adopts frame, paddle or propeller type blades for stirring and maintaining consistent temperature in the tank;

c) the autolysis temperature: the temperature of material after heating is maintained at 65° C.~95° C.;

d) Autolysis time: the time for the heating section to heat the materials to the target temperature should be less than 30 min, and the autolysis time in the holding section should be 30 min~360 min;

The sterilization adopts the microwave sterilization.

The temperature of materials after heating should be maintained at 65° C.~80° C. and the time of autolysis is 60~180 minutes.

Enzymic preparations can be added during autolysis to promote autolysis and improve the content of the autolysate. The enzymic preparations are proteases and the added amount is 0.5%~2.0% of material dry matter in the hydrolysis tank.

The specific method and steps are as follows:

(1) Precipitation and concentration: The bacterial proteins generating from the bioreactor are delivered to the settling thickener, and the bacterial proteins are precipitated at the bottom of the conical concentration tank. The material moisture content at the bottom is reduced to 97% or less for the subsequent dewatering process;

(2) convey the materials at the bottom of concentration tank to the centrifugal dewatering equipment using a transfer pump;

(3) Autolysis:

a) the said autolysis device is a vertical enzymatic reaction tank, by introducing he steam to the hydrolysis tank interlayer, it can achieve rapid heating, and then changing to injecting low-pressure steam for autolysis reaction;

b) the said autolysis device adopts frame, paddle or propeller type blades for stirring and maintaining consistent temperature in the tank;

c) the autolysis temperature: the temperature of material after heating is maintained at 65° C.~95° C.;

d) Autolysis time: the time for the heating section to heat the materials to the target temperature should be less than 30 min, and the autolysis time in the holding section should be 30 min~360 min;

(4) Drying: The materials after autolysis are conveyed to drying equipment for drying through a delivery pump; the said drying equipment is a spray drying equipment and the moisture content of materials after drying is 10~20%;

(5) Sterilization: The dried materials are conveyed to a tunnel type microwave drying sterilization equipment for sterilization by airflow lifting equipment; and the said materials after microwave sterilization have the moisture content at 5%~10%;

(6) Smashing and packaging: The sterilized materials can be packaged to finished products after smashing.

Enzymic preparations can be added during autolysis to promote autolysis and improve the content of the autolysate. The enzymic preparations are proteases and the added amount is 0.5%~2.0% of material dry matter in the hydrolysis tank.

A kind of aerobic-type single cell protein is produced by the above three methods. The moisture content of aerobic-type single cell protein producing by bacteria with protein content of 33%-60% is 5.0%40.0%; and the protein content is 33.0%-60.0%; the free nucleotides content per unit protein is not less than 1.40%; the free base content per unit protein is not higher than 0.90%; and the ratios of free bases to free nucleotides should be within the range of 0-0.60.

Compared with prior art, the process and products in the present invention have the following advantages:

1) Reflect that the SCP has endogenous enzymes, and make full use of the nuclease, protease, lysozyme in the bacterial protein in prior art;

2) Use the autolysis process. During the autolysis, macromolecular nutrients and cell walls are decomposed by autolytic enzymes, to produce high content of free amino acids, free nucleotides; besides, cell wall polysaccharides are decomposed and the cells produce permeability to ensure an active material can flow out of the cell which can be directly absorbed by animals;

3) The autolysis process may not need the extracellular water of bacterial protein, and endogenous enzymes can play a role in the intracellular micro-environment, thus, autolysis is adopted after centrifugal dewatering, to ensure high efficiency of autolysis and reduce the moisture content to be removed in the drying process after autolysis, thereby reducing the cost of drying;

4) The autolysis devices used can be heated quickly and the temperature is easy to control. The residence time of the material in the device can be controlled, to ensure that the autolysis of bacterial protein can be achieved under the optimal parameter condition;

5) The product digestibility is further improved after the autolysis process is used. The apparent digestibility of dry matter can be increased from 57.7% to 76.9%, and the protein apparent digestibility can be increased from 66.4% to 89.1%;

6) The products have high quality of proteins and the functional protein feed ingredients with a variety of active ingredients and physiological functions. The physiological functions include: attractant and improve feed intake, taste, odor improvement, immune function, hepatoprotective, anti-stress, prevent diarrhea, proteins of high quality and high digestibility. In animal experiments, it has better performance properties compared with the non-autolytic bacterial proteins;

7) The use of new production process further reduces the energy consumption, reasons are: a) the materials before drying is pre-heated during autolysis, enhancing the pre-drying temperature; b) the cell wall permeability of bacterial protein is increased after autolysis, the water and intracellular materials are easily flowed out, making it easier to drying;

8) The new process considers the autolysis, drying process in the post-processing, which is significantly higher than SCP culture and dewatering production capacity. The whole processing is divided into two sections. Connect the whole technological process with the efficient, temperature-controlled transport method, to give play to the production efficiency of all processing equipments, to significantly increase productivity and reduce repeated investment of equipments, thus, reducing costs.

BRIEF DESCRIPTION OF THE DRAWINGS

FIG. 3 shows the schematic of processing steps of aerobic-type single cell protein in Embodiment 2 in the invention;

FIG. 4 shows the schematic of processing steps of aerobic-type single cell protein in Embodiment 3 in the invention;

FIG. 5 shows the schematic of processing steps of aerobic-type single cell protein in Embodiment 4 in the invention;

Figure 1:
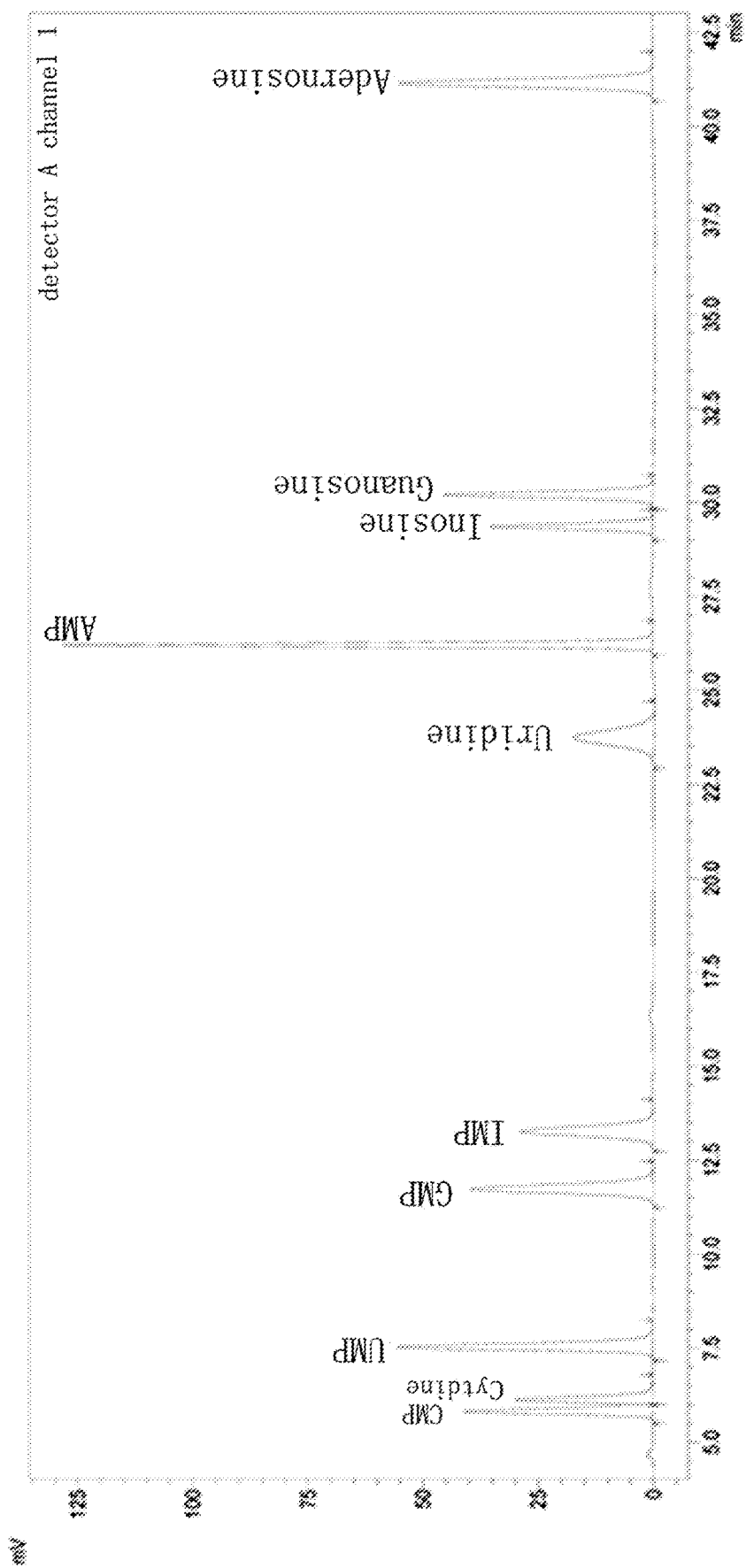
FIG. 1 shows the chromatogram of free nucleotides standard sample in Embodiment 1 in the invention.

Wherein, 1. pulley 2. reduction gear 3. transmission gear 4. cover pate 5. feeding port 6. heating hollow blade 7. insulation hollow blade 8. overflow plate 9. discharge port 10. inlet and outlet of steam 11. motor 12. host housing 13. drive spindle;

FIG. 3 is designated as the drawing attached to abstract in the invention.

DETAILED DESCRIPTIONS OF THE PREFERRED EMBODIMENTS

In the following, the present invention is described in details in combination with figures. The principle and equipments used in the method is very apparent for technicians skilled in the art. The specific embodiments herein are only used to explain, but not limited to, the present invention.

Embodiment 1: Establish the Detection Method of Free Nucleotides and Free Bases

The free nucleotides and free bases are used as autolysis process parameters, to adjust the main indicators before and after product autolysis. The principle is as follows: After autolysis and enzymolysis, yeast and bacterial proteins contain free nucleotides and bases, after extraction in aqueous solution, the samples enter the HPLC for analysis (C 18 column, UV detector, and buffer salt as mobile phase); and quantitative determination is performed for 5 kinds of nucleotides and 5 kinds of nucleosides, and 5 kinds of bases using the external standard method.

Free nucleotides refer to five kinds of nucleotides and five kinds of nucleosides, including cytidine monophosphate, uridine monophosphate, guanosine monophosphate, inosine monophosphate, adenosine, cytidine, uridine, inosine, guanosine, adenosine. Free bases refer to 5 kinds of nucleic acid bases, including cytosine, uracil, guanine, thymine and adenine.

SCP products contain rich nucleotides. The yeast products available on the markets are the main nucleotide providers in the feed industry. Due to the process characteristics, autolyzed yeast, zymolytic yeast and hydrolytic yeast contain more free nucleic acid hydrolyzates. Studies have shown that many yeast products contain free nucleotides and high content of bases. Free nucleotides can be quickly absorbed by animals, playing an important physiological function, but the base will produce adverse effect on the liver and kidney of animals. If there are excessive bases, enzymolysis, hydrolysis or microbial metabolism of nucleotides with important nutritional values have occurred in the production process, which will cause lower quality of yeast products. When the nucleotide content provided reduces, it can provide lower immune function of animals, besides, the increased base such as adenine will cause toxicity to animals. To judge the destruction of the nucleotides by the SCP production process and provide a scientific quality control assessment method that can reflect the process conditions and the nutritional value is extremely important. The free nucleotides represent the degree of autolysis. The higher, the degree of decomposition of nucleic acid to nucleotides is higher. Free bases are the product of bacterial metabolism; and the higher the content, the spoilage microbes grow more, which can be used as the indices for product spoilage after autolysis.

Reagents and Solutions:

Unless otherwise stated, all reagents used herein are AR, water is the deionized water, conforming to the requirements of Grade II water in GB/T 6682.

Potassium Dihydrogen Phosphate: AR.

Potassium hydroxide: AR.

Methanol: HPLC grade.

Acetonitrile: HPLC grade.

20% w/v potassium hydroxide solution: Weigh 100 g of potassium hydroxide, dissolved in 500 ml of water and stored in a volumetric flask.

Mobile phase A: 0.1M potassium dihydrogen phosphate. Weigh 27.2 g of potassium dihydrogen phosphate, dissolved in 1,000 ml of water, and add 1.0 ml of 20% potassium hydroxide solution, then add water to the constant volume of 2 L. After filtered by 0.45 um aquo-system filter membrane, the solution is reserved for standby.

Mobile phase B: 25% methanol solution. Fetch 250 ml methanol, dissolved in 750 ml water; after stirring and mixing well, filter a 0.45 um organic-system filter membrane for standby.

AMP: sigma #A2252.

CMP: sigma #C1131.

IMP: sigma #I2897.

GMP: sigma #G8377.

UMP: sigma #1752.

Adenosine: sigma #A9251.

Cytidine: sigma #C122106.

Guanosine: sigma #V900311.

Inosine: sigma #I4125.

Uridine: sigma #V900421.

Prepare standard mixed solution of nucleotide: Prepare the standard mixed solutions using UMP, AMP, GMP, CMP, IMP, guanosine, adenosine, uridine, inosine, cytidine separately, and the concentrations of each nucleotide are 20.000 ug/ml, 20.000 ug/ml, 20.000 ug/ml, 20.000 ug/ml, 20.00 ug/ml, 10.000 ug/ml, 10.000 ug/ml, 10.000 ug/ml, 10.000 ug within/ml, 10.000 ug/ml separately. Subpackage them in 0.5 ml cryopreserved vials at −20°C., which are valid for one year.

Cytosine: sigma #V900462.

Uracil: sigma #V900439.

Guanine: sigma #V900473.

Thymine: sigma #V900437.

Adenine: sigma #V900471.

Prepare the standard mixed solution of bases: Prepare the standard mixed solutions using cytosine, uracil, guanine, thymine, adenine separately, and the concentrations of the mixed standard base solutions are 16.00 ug/ml, 16.00 ug/ml, 20.00 ug/ml16.00 ug/ml 16.00 ug/ml separately. Subpackage them in 0.5 ml cryopreserved vials at −20°C., which are valid for one year.

Instruments and Equipments:

HPLC system (gradient elution, UV detection, controllable column temperature); Column: Athena C18,4.6×150 mm; analytical balance; centrifuge; ultrasonic cleaner; 1 mL disposable syringe; 0.45 um disposable water-phase filter; 0.5 ml centrifuge tube; 100 ml volumetric flask; 250 ml volumetric flask; 40 ml glass tube with lid; 1000 ul pipette; 5000 ul pipette; 15 mL plastic centrifuge tube.

Steps:

Sample Preparation:

(1) Weigh 0.1000 g sample in a 40 ml glass tube. Repeat sampling at least two groups for each sample.

(2) Add 15 ml water (dissolved volume, V), vortex shaking 3 times, 1 min each time, at an interval of 20 min each time.

(3) Ultrasound 20 min after shaking, and then vortex shaking again.

(4) Fetch 3 ml of test solution from the glass tube to a 5 ml centrifuge tube. Centrifuge 15 min at high speed 12000 g.

(5) Take 2 ml of supernatant to a 5 ml centrifuge tube, add 2 ml of water to dilute double. After mixed well, filter the solution and determine it in the machine.

Sample determination is performed by HPLC. The HPLC conditions are as follows:

| | |
|---|---|
| Ambient temperature | 25° C.~30° C. |
| Column | Athena C18, 4.6 × 150 mm |
| Detection wavelength | 260 nm |
| Column temperature | 30° C. |
| Mobile phase A | 0.1 mol/L potassium dihydrogen phosphate solution |
| Mobile phase B | 25% methanol |
| Injection volume | 20 ul |
| Flow rate | 0.5 mL/min |

(Note: washing the column with 100% acetonitrile solution after analysis for storage)

The elution procedure is shown in the table 1 below:

TABLE 1

| Gradient elution program | | |
|---|---|---|
| Time(min) | Phase A % | Phase B % |
| 0.00 | 100 | 0 |
| 15.00 | 100 | 0 |
| 15.01 | 60 | 40 |
| 28.00 | 60 | 40 |
| 28.01 | 40 | 60 |
| 40.00 | 40 | 60 |
| 42.00 | 0 | 100 |
| 55.00 | 0 | 100 |
| 55.01 | 100 | 0 |
| 70.00 | 100 | 0 |

Figure 2:
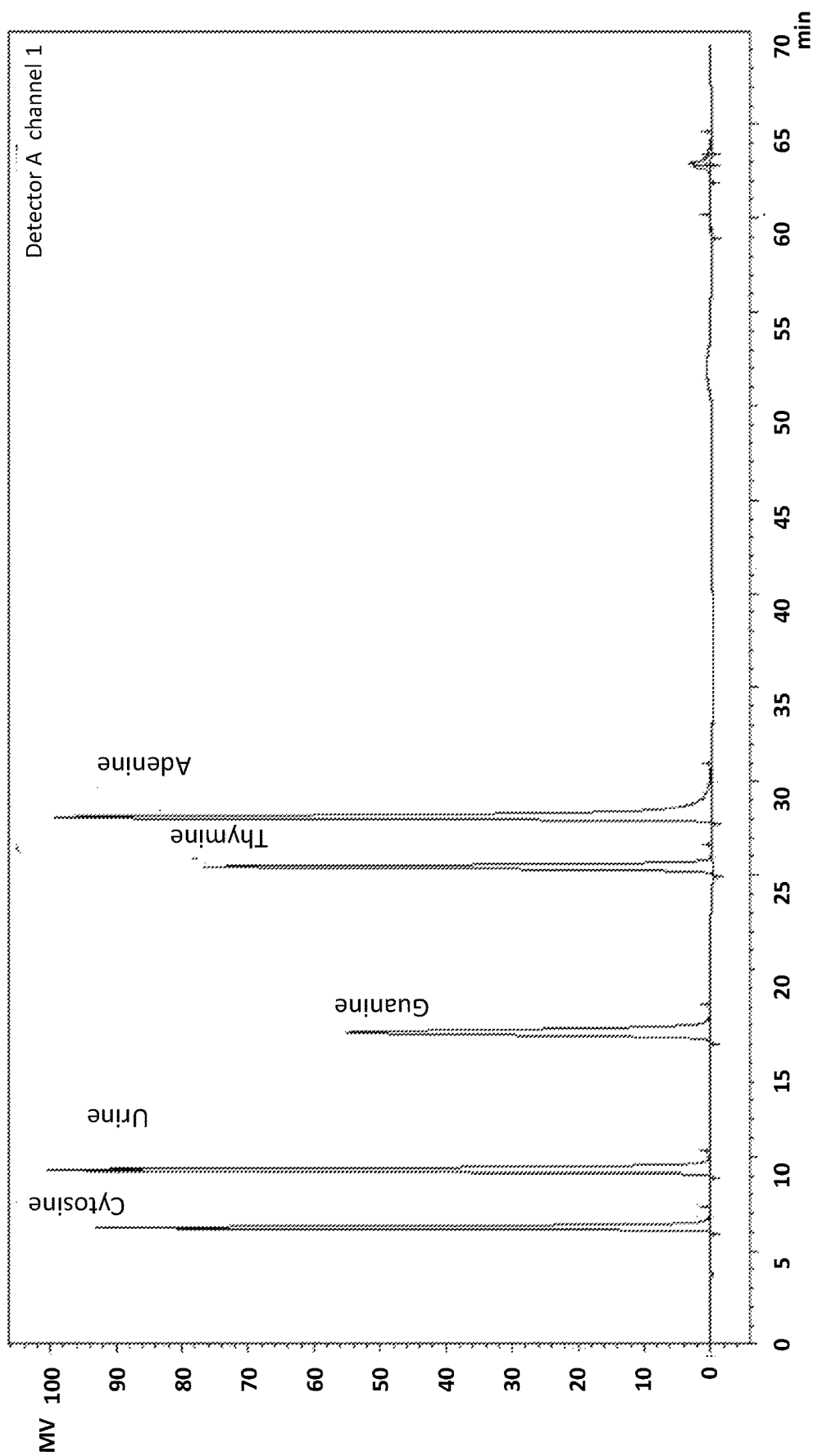
FIG. 2 shows the chromatogram of free base standard sample in Embodiment 1 in the invention.

As shown in FIG. 1 and FIG. 2, the several kinds of free nucleotides and bases can be separated using the above steps.

Calculation of Results:

The content of free nucleotides and bases in the sample is determined using the external standard method.

The content of bases, nucleosides and nucleotides ($\omega$) in the sample is indicated by mass fraction, in %, calculated according to the following formula:

$$C = \frac{A}{A_{st}} \times C_{st} \quad (1)$$

$$\omega_x = \frac{C \times V \times 2}{m \times 1000 \times 1000} \times 100 \quad (2)$$

Where:
A—the peak area of nucleotides, bases in the sample
$A_{st}$—the peak area of standard substance
$C_{st}$—the concentration of standard substance
x—a nucleotide or nucleoside or base
C—nucleotide concentration, ug/ml;
V—dissolved volume ml;
m—sample weight (g);
$\omega_x$—content %;

The results are expressed by the arithmetic mean of the parallel determination, rounded to two significant figures.

Precision:

Repeat the above detection. The absolute difference between twice independent determination results shall not exceed 10% of the arithmetic mean.

The contents of free bases and free nucleotides determined by the above method are shown in following table 2. As seen from the table, a high content of nucleotide can be available after the autolysis of product, which is higher than the commercially available yeast products.

TABLE 2

| Sample | Free nucleotide, % | Free base, % |
|---|---|---|
| Autolytic product I (50% protein) | 1.18 | 0.25 |
| Autolytic product II (35% protein) | 0.80 | 0.12 |
| Non- autolytic products | 0.10 | 0.00 |
| Commercially available beer yeast residue | 0.38 | 0.14 |
| Commercially available fish meal | 0.28 | 0.48 |
| Commercially available yeast I | 0.66 | 0.81 |
| Commercially available yeast II | 0.26 | 0.10 |
| Commercially available yeast III | 0.39 | 0.46 |

Embodiment 2: Autolysis Production Process and Products

The autolysis production process and product developed in the present invention includes but not limited to, the SCP product made according to the culture techniques in the patent WO2009059163A1. It also applies to the processing of three kinds of aerobic-type single cell protein products similar to the invention.

The processing of the first kind of aerobic-type single cell protein product includes the following steps:

1) Precipitation and concentration: Deliver the bacterial protein producing in the bioreactor to the settling thickener periodically, and the bacterial proteins are precipitated in the bottom of the conical concentration tank. When the material moisture content at the bottom is reduced to 97% or less, the subsequent dewatering step can be performed.

a) The diameter of tank in the embodiment is 15 meters, depth is 3.5 meters and effective volume is 477 cubic meters.

2) Convey the materials at the bottom of the concentration tank to the centrifugal dewatering equipment using a volumetric single-screw pump.

3) Centrifugal dewatering: The solid-liquid separation is performed using a horizontal spiral centrifuge. After centrifugation, the moisture content of material is reduced to 78%-82%, and the material is mud-like.

a) the material handling capacity of the centrifuge in this embodiment is 10-30 cubic meters/hour, the operating speed is 2000-3200 rev/min, the discharge amount is 1.5 tons/hour, and the solid content of feed is 3.0-5.0%. The solid content of supernatant ≤0.2% and the recovery rate of materials ≥95%.

4) Autolysis: The materials that extracellular water is removed by centrifuge are conveyed to the autolysis device for autolysis treatment;

a) The autolysis device in this embodiment is modified from twin-screw hollow blades dryer. By heating the hollow blades, the temperature for autolysis is achieved. The volume of the equipment chamber is 5.5 cubic meters, effective volume is 3~5.0 cubic meters, which is adjusted and controlled by the height of overflow plate.

b) The front ⅓ of the two twin-screw hollow blades of autolysis device in this embodiment is the heating section, which is heated by the steam at a pressure of 0.5-0.6 Mp. The remaining section is the holding section, and the temperature is maintained by 0.1 Mpa low-pressure steam and steam condensate of the front section after heating, to maintain the temperature for autolysis.

c) The autolysis temperature in this embodiment: the temperature of material after heating is maintained at 68° C.~80° C., preferably the autolysis temperature is 70° C.

d) Autolysis time in this embodiment: the time for the heating section to heat the materials to the target temperature should be less than 20 min, and the autolysis time in the holding section should be 160 min~200 min.

e) The moisture for materials in this embodiment: the material moisture content after autolysis should not be less than 70%.

The optimum temperature range for autolysis is achieved by the gradient test. The test parameters are as follows: the protein content of bacterial protein is 35.00%, the autolysis device is thermostat water bath, the moisture content of material is 82%, the autolysis time is 120 min. The range of autolysis temperatures is shown in the table below. After autolysis, the materials are reserved at −20° C. refrigerator for testing after microwave sterilization and drying.

As shown from the table 3 below, when the autolysis temperature is higher than 65° C., high content of free nucleotides can be produced by autolysis within 60 min. The content of free nucleotides is higher at 65° C.~70° C. within 60 min, and the content of free nucleotides is highest at 70° C. within 120 min.

TABLE 3

| Content of free nucleotides, % | | | | | | | | |
|---|---|---|---|---|---|---|---|---|
| | 55° C. | 60° C. | 65° C. | 70° C. | 75° C. | 80° C. | 85° C. | 90° C. |
| 0 min | 0.11 | 0.11 | 0.11 | 0.11 | 0.11 | 0.11 | 0.11 | 0.11 |
| 60 min | 0.23 | 0.34 | 0.53 | 0.54 | 0.50 | 0.42 | 0.53 | 0.49 |
| 120 min | 0.27 | 0.40 | 0.56 | 0.64 | 0.60 | 0.60 | 0.61 | 0.56 |

As shown from table 4 below, when autolysis at above 65° C., lower content of free bases may be produced within 60 min, indicating that the spoilage microbes do not grown in a large scale. The free content is highest at 60° C., while the free nucleotide content is not high, indicating that the free nucleotides have been used by spoilage microbes at this temperature, reducing the effect of autolysis.

TABLE 4

| Content of free bases, % | | | | | | | | |
|---|---|---|---|---|---|---|---|---|
| | 55° C. | 60° C. | 65° C. | 70° C. | 75° C. | 80° C. | 85° C. | 90° C. |
| 0 min | 0.02 | 0.02 | 0.02 | 0.02 | 0.02 | 0.02 | 0.02 | 0.02 |
| 60 min | 0.04 | 0.19 | 0.08 | 0.09 | 0.10 | 0.16 | 0.10 | 0.08 |
| 120 min | 0.08 | 0.22 | 0.13 | 0.13 | 0.14 | 0.14 | 0.11 | 0.12 |

As shown from the time gradient test data in table 5 and FIG. 6 below, bases will be produced continuously when autolysis at 60° C., suggesting that the spoilage microbes will continue to grow. At the time of 180 min-240 min, the content of free bases exceeds the content of free nucleotides and rancid flavor appears, indicating that the autolysis is poor at the temperature, mainly spoilage occurs.

TABLE 5

| 60° C. autolysis gradient | | |
|---|---|---|
| Time, min | Free bases, % | Free nucleotides, % |
| 0 | 0.03 | 0.14 |
| 60 | 0.19 | 0.34 |
| 120 | 0.22 | 0.40 |
| 180 | 0.25 | 0.44 |
| 240 | 0.42 | 0.20 |
| 300 | 0.42 | 0.20 |

As shown from the above test data, appropriate temperature for autolysis has a great influence on the product quality.

5) Drying: The materials after autolysis are conveyed to air flash drying equipment for drying through an auger feeder.

a) The material contact temperature for flash drying in this embodiment should be below 100° C.

b) The material moisture content after drying in this embodiment should be within the range of 15%-30%.

6) Sterilization: The dried materials are conveyed to a tunnel type microwave drying sterilization equipment for sterilization by airflow lifting equipment.

a) The total mold count and total bacterial count of material after microwave sterilization in this embodiment conform to the requirements in Hygiene standard for feeds (GB 13078-2001).

b) The moisture content of materials after microwave sterilization is 5%~10%.

7) Smashing and packaging: The sterilized materials can be packaged to finished products after smashing.

The SCP made through the above production process should meet the following quality indicators:

a) The free nucleotides content per unit protein should be higher than 1.40% b) The free base content per unit protein should be less than 0.90% c) The ratio of free bases to free nucleotides should be within the range of 0~0.60.

The key parameters of products obtained by bacterial protein with protein content of 35% through the above processing method are shown in the table 6 below:

TABLE 6

| Key Parameters | Result | Reference Value |
|---|---|---|
| Moisture content | 8.20% | ≤10.0% |
| Protein content (dry basis) | 35.20% | |

TABLE 6-continued

| Key Parameters | Result | Reference Value |
|---|---|---|
| Free nucleotides (dry basis) | 0.80% | |
| Free bases (dry basis) | 0.12% | |
| Free nucleotides (unit protein) | 2.27% | ≥1.40% |
| Free bases (unit protein) | 0.34% | ≤0.90% |
| Ratio of free bases to free nucleotides | 0.15 | 0~0.60 |

Embodiment 3: Autolysis Production Process and Products

Another processing method of aerobic-type single cell protein product, which is divided into two parts, completed by different production units respectively, of which, the first part is the pre-processing unit, including the process from precipitation and concentration to centrifugal dewatering after completing SCP culture. This part can set up multiple pre-processing units, such as 2-10 units. The second part is post-processing unit, comprising the autolysis, drying, sterilization operations. The first part and the second part is achieved by a transport way. In this part, a post-processing unit is set up.

When only one pre-processing unit is set up, the pre-processing unit and the post-processing unit can be an integral part.

When two or more pre-processing units are set up, the pre-processing unit and the post-processing unit are separated each other.

The distance between the pre-processing unit and the post-processing unit is 0~500 km, preferably within 400 km.

As shown in the figure, three pre-processing units and one post-processing unit are set up in this embodiment.

Following steps are completed in the pre-processing unit:

1) Precipitation and concentration: Deliver the bacterial protein producing in the bioreactor to the settling thickener periodically, and the bacterial proteins are precipitated in the bottom of the conical concentration tank. When the material moisture content at the bottom is reduced to 97% or less, the subsequent dewatering step can be performed.

a) The diameter of tank in the embodiment is 15 meters, depth is 3.5 meters and effective volume is 477 cubic meters.

2) Convey the materials at the bottom of the concentration tank to the centrifugal dewatering equipment using a volumetric single-screw pump.

3) Centrifugal dewatering: The solid-liquid separation is performed using a horizontal spiral centrifuge. After centrifugation, the moisture content of material is reduced to 78%-82%, and the material is mud-like.

a) the material handling capacity of the centrifuge in this embodiment is 10-30 cubic meters/hour, the operating speed is 2000-3200 rev/min, the discharge amount is 1.5 tons/hour, and the solid content of feed is 3.0-5.0%. The solid content of supernatant ≤0.2% and the recovery rate of materials ≥95%.

4) Transport: After centrifugation, the materials are cooled down and transported to the post-processing unit for centralized treatment.

a) The temperature of material is cooled down to below 5° C. before transport in this embodiment.

b) In this embodiment, the mud-like material producing from the pre-processing unit is delivered to the post-processing unit for subsequent processing by an insulation truck.

c) In this embodiment, the distance from three pre-processing units to the post-processing unit is less than 300 km, and the time of transport is within 4 hours. The temperature of materials arriving at the post-processing unit is not higher than the temperature of material leaving the pre-processing unit by 4° C.

The time of transport is determined by the tests of samples at different temperature and different times. The protein content of autolytic material is 50%, moisture content is 82%. The samples are stored at different test temperature and different storage times before autolysis. The conditions for autolysis: temperature 70° C. and time 180 min. Test results are shown in the table below.

As seen from table 7, the product autolysis occurs when placed within 15 hours at below 10° C., but it will not cause abnormal nucleotides and bases, indicating that the enzyme activity of bacterial protein and harmful bacteria when preserved below 0° C. will not have significant changes. The transport of bacterial protein within a certain time at this temperature will not cause influence on the products.

TABLE 7

| Holding Temperature | Holding Time | Free nucleotides, % | Free bases, % |
|---|---|---|---|
| 5° C. | 1 h | 1.22 | 0.27 |
|  | 5 h | 1.23 | 0.27 |
|  | 10 h | 1.22 | 0.24 |
|  | 15 h | 1.24 | 0.26 |
| 10° C. | 1 h | 1.21 | 0.24 |
|  | 5 h | 1.23 | 0.27 |
|  | 10 h | 1.20 | 0.27 |
|  | 15 h | 1.22 | 0.29 |
| 15° C. | 1 h | 1.20 | 0.29 |
|  | 5 h | 1.23 | 0.28 |
|  | 10 h | 1.20 | 0.31 |
|  | 15 h | 1.08 | 0.46 |
| 25° C. | 1 h | 1.19 | 0.30 |
|  | 5 h | 1.11 | 0.38 |
|  | 10 h | 1.02 | 0.47 |
|  | 15 h | 0.96 | 0.55 |

The following steps are completed in the post-processing unit:

5) Autolysis: The materials from 3 pre-processing units are conveyed to the insulation silo, and then conveyed to autolysis device for autolysis treatment.

a) The autolysis device in this embodiment is modified from twin-screw hollow blades dryer in this embodiment. By heating the hollow blades, the temperature for autolysis is achieved. The volume of the equipment chamber is 7.5 cubic meters, effective volume is 5.0~7.0 cubic meters, which is adjusted and controlled by the height of overflow plate. The autolysis device can meet the production of materials in 3 pre-processing units in the embodiment.

b) The front ⅓ of the two twin-screw hollow blades of autolysis device in this embodiment is the heating section, which is heated by the steam at a pressure of 0.5-0.6 Mp. The remaining section is the holding section, and the temperature is maintained by 0.1 Mpa low-pressure steam and steam condensate of the front section after heating, to maintain the temperature for autolysis.

c) The autolysis temperature in this embodiment: the temperature of material after heating is maintained at 68° C.~80° C., preferably the autolysis temperature is 70° C.

d) Autolysis time in this embodiment: the time for the heating section to heat the materials to the target temperature should be less than 20 min, and the autolysis time in the holding section should be 60 min~90 min.

e) The moisture for materials in this embodiment: the material moisture content after autolysis should not be less than 70%.

6) Drying: The materials after autolysis are conveyed to air flash drying equipment for drying through an auger feeder.

a) The material contact temperature for flash drying in this embodiment should be below 100° C.

b) The material moisture content after drying in this embodiment should be within the range of 15%-30%.

7) Sterilization: The dried materials are conveyed to a tunnel type microwave drying sterilization equipment for sterilization by airflow lifting equipment.

a) The total mold count and total bacterial count of material after microwave sterilization in this embodiment conform to the requirements in Hygiene standard for feeds (GB 13078-2001).

b) The moisture content of materials after microwave sterilization is 5%~10%.

8) Smashing and packaging: The sterilized materials can be packaged to finished products after smashing.

The SCP made through the above production process should meet the following quality indicators:

a) The free nucleotides content per unit protein should be higher than 1.40% b) The free base content per unit protein should be less than 0.90% c) The ratio of free bases to free nucleotides should be within the range of 0~0.60.

The key parameters of products obtained by bacterial protein with protein content of 50% through the above processing method are shown in the table 8 below:

TABLE 8

| Key Parameters | Result | Reference Range |
| --- | --- | --- |
| Moisture content | 9.40% | ≤10.0% |
| Protein content (dry basis) | 50.70% | |
| Free nucleotides (dry basis) | 0.80% | |
| Free bases (dry basis) | 0.12% | |
| Free nucleotides (unit protein) | 2.64% | ≥1.40% |
| Free bases (unit protein) | 0.34% | ≤0.90% |
| Ratio of free bases to free nucleotides | 0.15 | 0~0.60 |

Embodiment 4: Autolysis Production Process and Products

The processing method of the third kind of aerobic-type single cell protein product comprises the following steps:

1) Precipitation and concentration: Deliver the bacterial protein producing in the bioreactor to the settling thickener periodically, and the bacterial proteins are precipitated in the bottom of the conical concentration tank. When the material moisture content at the bottom is reduced to 98% or less, the subsequent dewatering step can be performed.

a) The diameter of tank in the embodiment is 15 meters, depth is 3.5 meters and effective volume is 477 cubic meters.

2) Autolysis: The materials at the bottom of the concentration tank are conveyed to the autolysis device.

a) The autolysis device is vertical enzymatic reaction tank in this embodiment. The device parameters: volume of 5000 L, the heat transfer area of 13.5 square meters, stirring power of 4.0 kilowatts, the form of stirring blades is frame type, and heating of jacket with saturated steam.

b) The temperature of autolysis in this embodiment: the temperature of material after heating is maintained at 65° C.~95° C., preferably the autolysis temperature is 65° C.~80° C., and more preferably 70° C.

c) Autolysis time in this embodiment: the time from the heating stage to the target temperature should be less than 30 min after the materials are pumped to the hydrolysis tank, preferably less than 20 min. The time of autolysis in the temperature holding stage should be 90 min.

The optimum temperature range for autolysis is achieved by the gradient test. The test parameters are as follows: the protein content of bacterial protein is 35.00%, the autolysis device is thermostat water bath, the moisture content of material is 82%, the autolysis time is 120 min. The range of autolysis temperatures is shown in the table 3. After autolysis, the materials are reserved at −20° C. refrigerator for testing after microwave sterilization and drying.

As shown from the table 3 in the embodiment 2, when the autolysis temperature is higher than 65° C., high content of free nucleotides can be produced by autolysis within 60 min. The content of free nucleotides is higher at 65° C.~70° C. within 60 min, and the content of free nucleotides is highest at 70° C. within 120 min.

As shown from table 4 in the embodiment 2, when autolysis at above 65° C., lower content of free bases may be produced within 60 min, indicating that the spoilage microbes do not grown in a large scale. The free content is highest at 60° C., while the free nucleotide content is not high, indicating that the free nucleotides have been used by spoilage microbes at this temperature, reducing the effect of autolysis.

Figure 6:
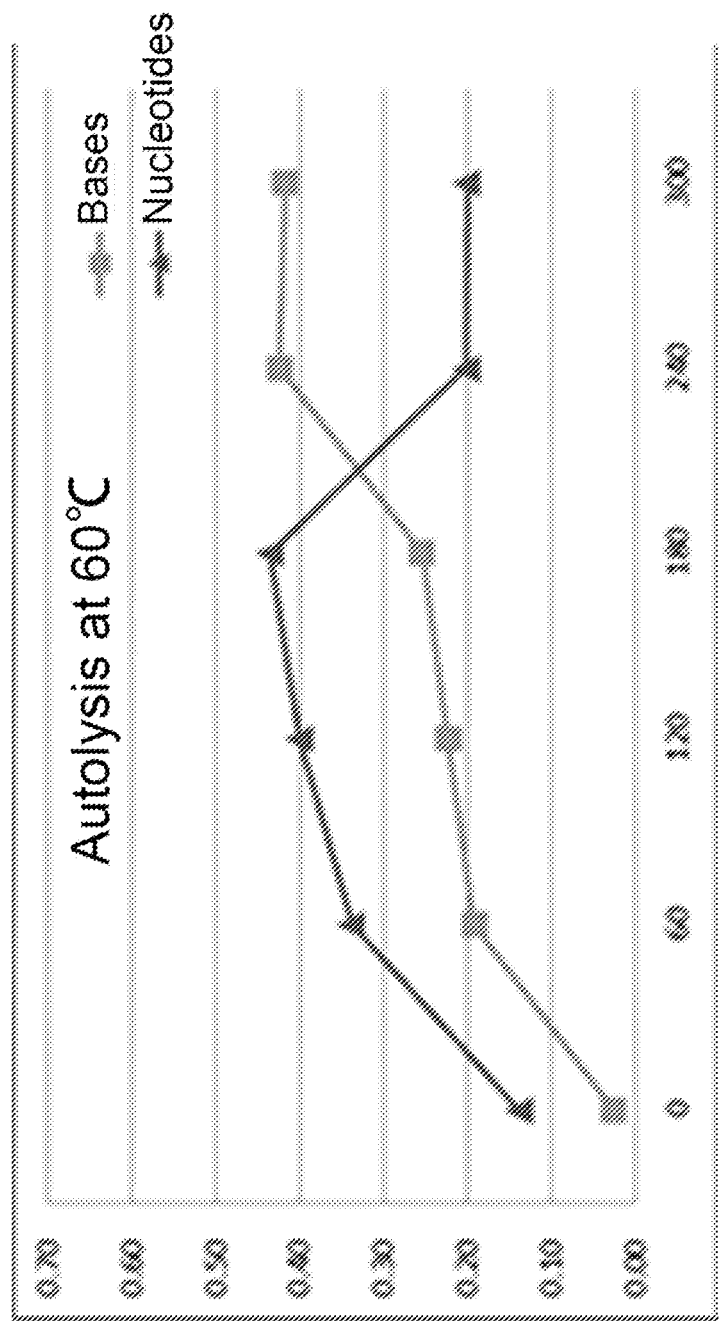
FIG. 6 shows the metering measurement chart of bases and nucleotides at 60° C. autolysis in Embodiment 2 and Embodiment 4 in the invention.
Figure 7:
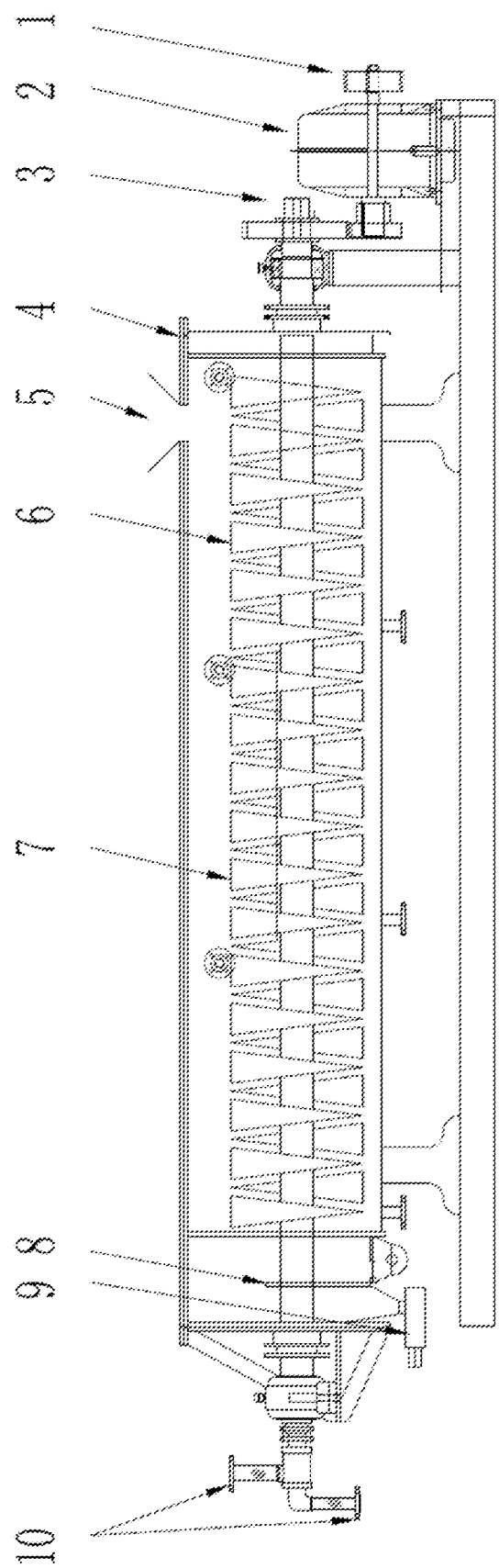
FIG. 7 shows the front view of autolysis device in Embodiment 2 and Embodiment 3 in the invention.
Figure 8:
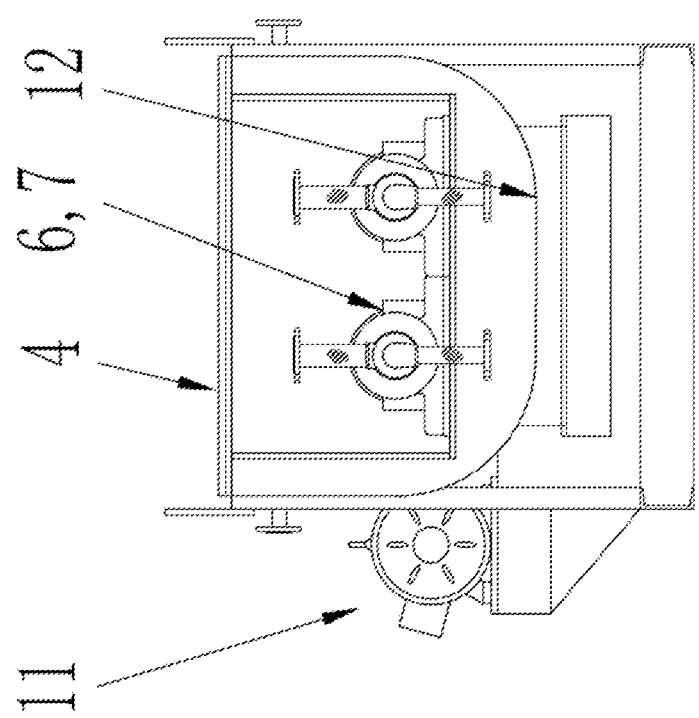
FIG. 8 shows the side view of autolysis device in Embodiment 2 and Embodiment 3 in the invention.
Figure 9:
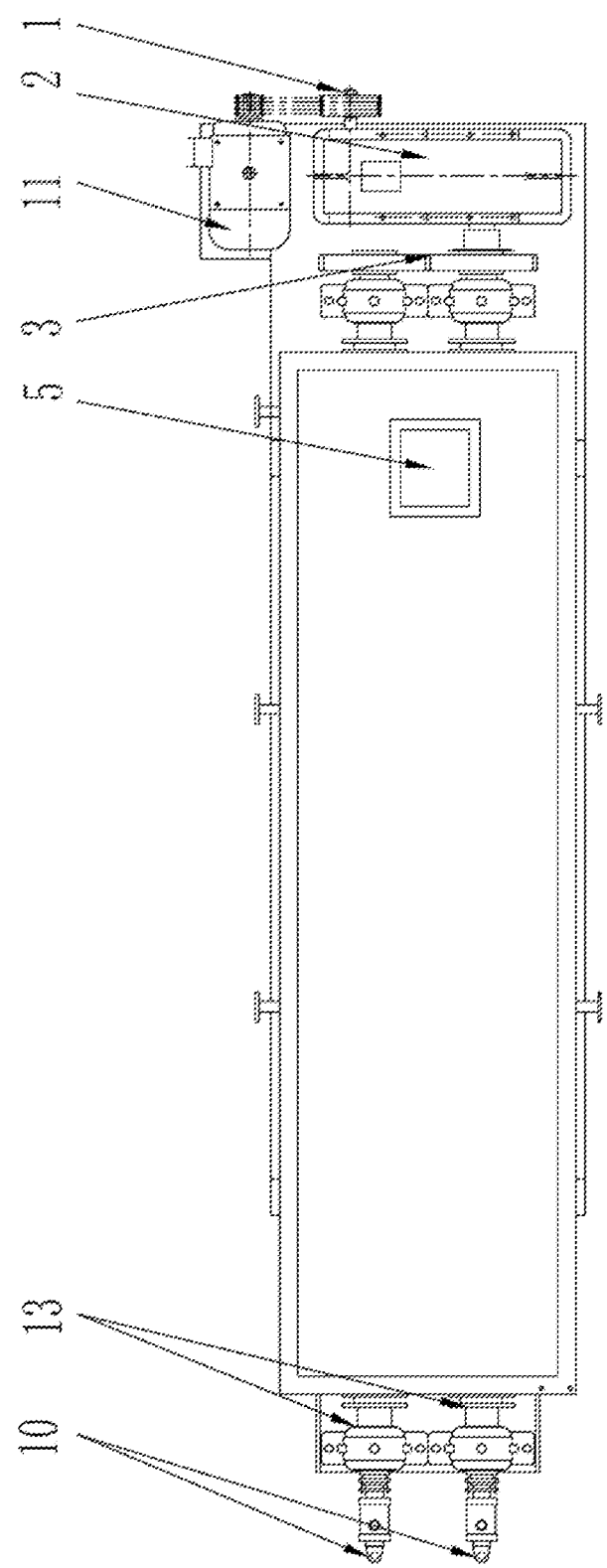
FIG. 9 shows the Bird's-eye view of autolysis device in Embodiment 2 and Embodiment 3 in the invention.

As shown from the time gradient test data in table 5 and FIG. 6 in the embodiment 2, bases will be produced continuously when autolysis at 60° C., suggesting that the spoilage microbes will continue to grow. At the time of 180min-240 min, the content of free bases exceeds the content of free nucleotides and rancid flavor appears, indicating that the autolysis is poor at the temperature, mainly spoilage occurs.

As shown from the above test data, appropriate temperature for autolysis has a great influence on the product quality.

3) Drying: The materials after autolysis are conveyed to drying equipment for drying through a delivery pump.

a) The drying equipment can be spray drying equipment.

b) The material moisture content after drying is within the range of 10~20%.

4) Sterilization: The dried materials are conveyed to a tunnel type microwave drying sterilization equipment for sterilization by airflow lifting equipment.

a) The total mold count and total bacterial count of material after microwave sterilization conform to the requirements in Hygiene standard for feeds (GB 13078-2001).

b) The moisture content of materials after microwave sterilization is 5%~10%.

5) Smashing and packaging: The sterilized materials can be packaged to finished products after smashing.

The SCP made through the above production process should meet the following quality indicators:

a) The free nucleotides content per unit protein should be higher than 1.40% b) The free base content per unit protein should be less than 0.90% c) The ratio of free bases to free nucleotides should be within the range of 0~0.60.

The key parameters of products obtained by bacterial protein with protein content of 40% through the above processing method are shown in the table 9 below.

TABLE 9

| Key Parameters | Result | Reference Value |
| --- | --- | --- |
| Moisture content | 9.3% | ≤10.0% |
| Protein content (dry basis) | 40.90% | |
| Free nucleotides (dry basis) | 0.95% | |
| Free bases (dry basis) | 0.31% | |
| Free nucleotides (unit protein) | 2.32% | ≥1.40% |
| Free bases (unit protein) | 0.76% | ≤0.90% |
| Ratio of free bases to free nucleotides | 0.33 | 0~0.60 |

Embodiment 5: Digestibility Test

The differences in the apparent digestibility between the bacterial protein with autolysis process and ordinary bacterial protein are evaluated through the animal tests.

The digestibility refers to the percentage of digestible nutrients among the eatable feed nutrients. The indicator method is used. Using the indicators existing in the feed or artificially added, calculate the digestibility according to the unit indicator contained in unit feed and feces after feeding the fishes. The formulations are prepared according to the digestible nutrients in feed raw material, which have great significance for enhancing the feed digestion and utilization and reducing the contamination of feed substances on the breeding water environment.

Test Protocol:

Assessment of raw materials: The bacterial protein with the protein content of 50% is produced by the autolysis process according to the method in the embodiments 2-4. The ordinary non-autolytic protein with content of 50% is the same batch of SCP.

Test feed is composed of "70% basal feed+30% test material". Add 0.01% yttrium oxide to the test feed as the indicator, which is evenly mixed in the feed powder by stepwise diffusion method. When preparing the test feeds, all raw materials should pass 40-mesh. Prepare the pellet feed with the particle size of 3 mm using a pelleter.

The test is performed in a 145 L plastic aquarium. The water is aerated tap water. The aquarium is filled with gas using oxygenation pump, and the temperature of the aquarium is controlled using heating rods. ⅔ of water is changed every day, to keep the water clean. During the test, the water temperature is 15±1° C., pH is 6.5-7.5, and dissolved oxygen>4.0 mg/l. The test fish is rainbow trout.

Three test groups are set, including one basal feed group and two test feed groups. 3 repeats are established in each group, a total of 9 aquariums, each aquarium contains 50 fishes.

After acclimation for 7 days in the aquarium, the test fishes are fed test feeds; 7 days later, formal test is carried out. During the test, feed twice every day (8:30; 15:30), and suck out the residual feeds using a siphon 0.5 hour after feeding each time. Collect the fish feces during the peak of defecation every day, and promptly take out the feces using a dense screen mesh each time, and then pick up the feces with complete membrane to the Petri dish using the forceps, dry in an oven at 70° C. to constant weight, then place the feces to a dryer until the feces are enough for testing.

Calculation of Results:

The apparent digestibility of dry matter and protein in test feed and basal feed is calculated as follows:

The apparent digestibility of dry matter (%)=100×(1−B/B')

The apparent digestibility of nutrients (%)=[1−(A'/A)×(B/B')]×100

Where, A,B are the nutrient and yttria content in the feed respectively, A', B' are the corresponding nutrient and yttria content in the feces respectively.

The apparent digestibility of feed dry matter, protein and amino acids is calculated according to the following formula [1, 2, 3,]:

$$\text{digestibility} 消化率 /\% = \frac{DT - rDR}{1-r}$$

Where: DT and DR are the digestibility of nutrients in the test feed and basal feed $$r = \frac{\text{Weigh of basal feed in the test feed}}{\text{Weight of test feed}} \times \frac{\text{The content of a nutrient in basal feed}}{\text{The content of a nutrient in test feed}}$$

Results: The digestibility test data are shown in the following tables 10-12.

TABLE 10

The apparent digestibility of dry matter and protein in bacterial proteins in different processing techniques

| Feed | Dry matter, % | Protein, % |
|---|---|---|
| Autolytic SCP | 76.9 | 89.1 |
| Non-autolytic SCP | 57.7 | 66.4 |

TABLE 11

The apparent digestibility of dry matter and protein in bacterial proteins in different processing techniques

| Feed | Dry matter, % | Protein, % |
|---|---|---|
| Autolytic SCP | 78.3 | 90.0 |
| Non-autolytic SCP | 56.8 | 65.4 |

TABLE 12

The apparent digestibility of dry matter and protein in bacterial proteins in different processing techniques

| Feed | Dry matter, % | Protein, % |
|---|---|---|
| Autolytic SCP | 80.2 | 93.0 |
| Non-autolytic SCP | 55.7 | 65.5 |

As shown from above table 11 and table 12, the digestibility of dry matter and protein of SCP using the autolysis process is significantly enhanced, indicating that the bacterial cell wall is fully broken after autolysis, and the nucleotides, proteins and other nutrients are free outside the cell, thus, it is more easily to absorb them by animals.

Embodiment 6: Feed Intake Test

Assess the difference in the attractant and feed intake between the bacterial protein with autolysis process and the ordinary bacterial protein by using the double trough preference test in piglets. The double trough preference test in piglets can be used to determine the preference of piglets in particular flavor of feeds. For piglets, the feed intake can be increased by feeding the preferred feeds, and thus increasing the growth rate.

Test Program:

Assessment materials: 50% autolytic SCP, ordinary non-autolytic protein is also 50% SCP. Test feed: the basal diet is the commercially available weaned piglet feed, and the ratio of test feed is shown in the table.

Test animals: select 45 healthy weaned piglets with similar weaning age and body weight, normal feeding, and randomly divide them into 3 groups.

TABLE 13

| No. | feed A | feed B |
|---|---|---|
| Feed | Basal feed | |
| Item | Non-autolytic SCP | Autolytic SCP |
| Additive amount | 2% | 2% |
| Feed amount | 100 kg | 100 kg |

Test Method:

Put 2 troughs of the same level and specification in the same pigsty (the level of feed in each trough must be the same as the quantity of the test pig), place a certain amount of test feed in the troughs respectively (the amount of feed must be enough, to guarantee two hours' diets). Add feed A in trough A and add feed B in the trough B. pigs freely take feeds for 2 hours, collect the remaining feed in the trough, and measure them, then add feed B in trough A and add feed A in trough B, to perform the same test.

During the test, observe the quantity of the pigs that take the feeds in the two troughs, and track their feed intake and the change of quantity of pigs by filming with a video camera and a camera. Requirements: the test must be performed 3-4 times continuously, and 3-4 repeats each time. A total of 3-5 days or until the end of feed intake.

Calculation of Results:

Indicators: Feed intake and addicted index:

Addicted index of feed A=The total dietary intake in group A/The total dietary intake in group B

| Feed | Feed intake, g | Addicted index |
| --- | --- | --- |
| Feed A | 1040 | 0.82 |
| Feed B | 1258 | 1.21 |

The test results showed that, under the test condition in the embodiment, the weaned piglets have preference to autolytic SCP and have high feed intake. The autolyzed free nucleotides showed attractant effect.

What is claimed is:

1. A method for producing an aerobic-type single cell protein from materials by an autolysis, comprising the following steps:
   (1) delivering bacterial proteins generated from a bioreactor to a conical concentration tank, and precipitating the bacterial proteins at the bottom of the conical concentration tank, wherein the material moisture content at the bottom is reduced to 97% or less for the subsequent dewatering process;
   (2) pumping the materials at the bottom of the concentration tank to centrifugal dewatering equipment by a transfer pump;
   (3) performing a solid-liquid separation using a horizontal spiral centrifuge, wherein the material moisture content is reduced to 78% to 85% and the materials are mud-like after the centrifugation;
   (4) transferring the materials from step (3) to an autolysis device comprising twin-screw hollow blades, wherein the front ¼ to ½ of the twin-screw front hollow blade of the autolysis device is a heating section and the remaining section is a holding section and the device is preheated through the twin-screw hollow blades to an autolysis temperature of between 65° C. and 95° C. for a preheating time of 5 to 30 min; and carrying out an autolysis, comprising maintaining the materials in the autolysis device at a temperature between 65° C. and 95° C. for a time of 30 to 360 min;
   (5) conveying the materials resulting from the autolysis through an auger feeder to air flash drying equipment for drying; wherein the contact temperature of the materials is between 65 and 100° C. and the moisture content of the materials after drying is between 10% and 40%;
   (6) conveying the materials from step (5) to a tunnel type microwave drying sterilization apparatus by airflow lifting equipment for sterilization; wherein said materials after the microwave sterilization have a moisture content between 5% and 10%; and
   (7) smashing and packaging the materials from step (6); wherein the aerobic-type single cell protein has 33%-60% of protein, 0.1-1.4% free nucleotides, and 0-0.9% free base, and the ratio of free bases to free nucleotides is between 0 to 0.60.

2. The method according to claim 1, wherein the temperature of materials is maintained between 65° C. and 80° C. during the autolysis and the time for autolysis is between 60 and 180 minutes.

3. The method according to claim 1, wherein a pre-processing step is carried out before step (4) comprising: decreasing the temperature of the materials from step 3 below 10° C. in a pre-processing segment, and transporting the cooled materials to the autolysis device for subsequent processing, wherein the time of said transport is between 0 and 12 hours, and the temperature of the materials arriving at the autolysis device is no more than 5° C. higher than the temperature when leaving the pre-processing segment.

* * * * *